United States Patent
Rose et al.

(10) Patent No.: US 9,560,970 B2
(45) Date of Patent: Feb. 7, 2017

(54) SYSTEMS AND METHODS FOR INTEGRATION OF A POSITRON EMISSION TOMOGRAPHY (PET) DETECTOR WITH A COMPUTED-TOMOGRAPHY (CT) GANTRY

(71) Applicant: General Electric Company, Schenectady, NY (US)

(72) Inventors: Timothy Patrick Rose, Pewaukee, WI (US); Michael D. Maki, Oconomowoc, WI (US); Chad Allan Smith, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 216 days.

(21) Appl. No.: 13/938,020

(22) Filed: Jul. 9, 2013

(65) Prior Publication Data

US 2015/0018673 A1    Jan. 15, 2015

(51) Int. Cl.
*A61B 5/00*    (2006.01)
*A61B 6/03*    (2006.01)
*G01T 1/29*    (2006.01)
*A61B 6/00*    (2006.01)

(52) U.S. Cl.
CPC ............ *A61B 5/0035* (2013.01); *A61B 6/032* (2013.01); *A61B 6/035* (2013.01); *A61B 6/037* (2013.01); *G01T 1/2985* (2013.01); *A61B 6/4258* (2013.01); *A61B 6/5247* (2013.01)

(58) Field of Classification Search
None
See application file for complete search history.

(56) References Cited

U.S. PATENT DOCUMENTS

| | | | |
|---|---|---|---|
| 2003/0058984 A1* | 3/2003 | Susami et al. | 378/19 |
| 2004/0260171 A1* | 12/2004 | Graumann | 600/411 |
| 2010/0001156 A1 | 1/2010 | Stefan | |
| 2011/0077511 A1* | 3/2011 | Kim | A61B 6/032 600/427 |
| 2012/0001077 A1* | 1/2012 | Inoue et al. | 250/363.02 |
| 2012/0265050 A1 | 10/2012 | Wang | |

FOREIGN PATENT DOCUMENTS

DE    102009014619 A1    10/2010

OTHER PUBLICATIONS

Wang et al. "Towards Omni-Tomography-Grand fusion of Multiple modalities for simultaneous interior tomography", PloS One, Jun. 2012, vol. 7, Issue 6, e39700 pp. 1-12.*
Search Report and Written Opinion from Corresponding PCT application No. PCT/US2014/045654 dated Oct. 10, 2014. 10 pages.

* cited by examiner

*Primary Examiner* — Long V Le
*Assistant Examiner* — Marjan Saboktakin
(74) *Attorney, Agent, or Firm* — Dean D. Small; The Small Patent Law Group, LLC.

(57) ABSTRACT

Systems and methods for integration of a PET detector with a CT gantry are provided. One system includes an x-ray computed tomography (CT) gantry having a rotating portion and a stationary portion within a housing, and including a bore volume therethrough. The system also includes an x-ray source and an x-ray detector coupled to the rotating portion. The system further includes a positron emission tomography (PET) detector, wherein the PET detector is coupled to the stationary portion of the CT gantry, such that the PET detector extends at least partially into the CT gantry with at least a portion of the PET detector within the housing of the CT gantry.

20 Claims, 4 Drawing Sheets

SYSTEMS AND METHODS FOR INTEGRATION OF A POSITRON EMISSION TOMOGRAPHY (PET) DETECTOR WITH A COMPUTED-TOMOGRAPHY (CT) GANTRY

BACKGROUND OF THE INVENTION

Embodiments described herein generally relate to imaging systems, particularly to multi-modality imaging systems, such as positron emission tomography (PET)/computed tomography (CT) systems.

CT imaging systems typically include an x-ray source and a detector. In operation, the x-ray source and the detector are rotated around the object to be imaged such that an angle at which an x-ray beam intersects the object changes. A group of x-ray attenuation measurements, or projection data, from a detector at one gantry angle may be referred to as a "view." A set of views made at different gantry angles during one revolution of the x-ray source and detector may be referred to as a "scan." In an axial scan, projection data is processed to construct an image that corresponds to a two-dimensional cross-section or slice of an object being scanned.

PET imaging systems may scan objects to acquire image information using non-moving detectors. During operation of a PET imaging system, for example, a patient is initially injected with a radiopharmaceutical that emits positrons as the radiopharmaceutical decays. The emitted positrons travel a relatively short distance before the positrons encounter an electron, at which point an annihilation event occurs whereby the electron and positron are annihilated and converted into two gamma photons that are detected using scintillators, arranged in a ring within an annular gantry. Signals from the scintillators are then processed to produce an image.

It can be beneficial to utilize both CT and PET systems to scan a subject such as in known dual-modality imaging systems. Separate gantries are used in these dual-modality imaging systems. However, having two imaging detector gantries (in tandem) increases the footprint of the system and consequently a larger imaging room is needed. Further, newer CT detectors have an increasingly higher field of view, which increase the CT detector size. The larger CT detector in these dual-modality CT/PET systems results in the PET detector being displaced further along into the bore volume. Thus, the patient travels further into the bore volume, which can cause claustrophobia and general discomfort for certain patients. In addition, as a result of the increased travel length, the patient table has to be made stronger with additional reinforcements.

Some known dual-modality imaging systems attempt to reduce the distance between detectors of the different modalities. For example, some systems co-locate the PET detectors and the CT detectors on a common rotating portion of the gantry. However, it is not always desirable to rotate the PET ring. Other systems position the CT and PET detectors side by side and provide a moving patient platform. However, this arrangement increases the difficulty of co-registration and alignment.

SUMMARY OF THE INVENTION

In one embodiment, an imaging system is provided that includes an x-ray computed tomography (CT) gantry having a rotating portion and a stationary portion within a housing, and including a bore volume therethrough. The imaging system also includes an x-ray source and an x-ray detector coupled to the rotating portion. The imaging system further includes a positron emission tomography (PET) detector, wherein the PET detector is coupled to the stationary portion of the CT gantry, such that the PET detector extends at least partially into the CT gantry with at least a portion of the PET detector within the housing of the CT gantry.

In another embodiment, an imaging system is provided that includes an x-ray computed tomography (CT) gantry having a rotating portion and a stationary portion within a housing and including a bore volume therethrough. The imaging system also includes an x-ray source and an x-ray detector coupled to the rotating portion. The imaging system further includes a positron emission tomography (PET) gantry having a PET detector ring coupled thereto. The PET gantry is coupled to the stationary portion of the CT gantry, and the PET detector ring extends at least partially into the CT gantry, such that at least a portion of the PET detector ring is within the housing of the CT gantry.

In yet another embodiment, an imaging system is provided that includes an x-ray computed tomography (CT) gantry having a rotating portion and a stationary portion within a housing and including a bore volume therethrough. The bore volume has a constant diameter along a length of an examination axis through the CT gantry. The imaging system also includes; an x-ray detector coupled to the rotating portion of the CT gantry and a positron emission tomography (PET) detector ring coupled to the stationary portion of the CT gantry, wherein the PET detector ring extends at least partially into the CT gantry.

DETAILED DESCRIPTION OF THE INVENTION

The following detailed description of certain embodiments will be better understood when read in conjunction with the appended drawings.

Furthermore, references to "one embodiment" are not intended to be interpreted as excluding the existence of additional embodiments that also incorporate the described features. Moreover, unless explicitly stated to the contrary, embodiments "comprising" or "having" an element or a plurality of elements having a particular property may include additional such elements not having that property. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide imaging systems that employ a variety of imaging techniques to generate images. For example, positron emission tomography (PET) imaging systems may be used that generate images depicting the distribution of positron-emitting nuclides in patients based on coincidence emission events detected using a detector system, usually configured as a ring assembly of detector blocks. The positron interacts with an electron in the body of the patient by annihilation, and then the electron-positron pair is converted into two photons. The photons are emitted in opposite directions along a line of response. The annihilation photons are detected by detectors on both sides of the line of response of a detector ring. The image is then generated based on the acquired emission data that includes the annihilation photon detection information.

Various embodiments also include computed tomography (CT) imaging system. For example, CT imaging systems include a gantry having a rotating portion and a stationary portion. The rotating portion includes an x-ray source that projects a beam of x-rays onto a set of x-ray detectors on the opposite side of the ring that acquire image data to generate images. A slip ring is used to connect the detectors to the stationary portion of the CT gantry.

In various embodiments, a dual modality imaging system is provided wherein the imaging system allows for multiple scans in different modalities to facilitate an increased diagnostic capability over single modality systems. Although various embodiments are described in the context of an exemplary dual modality imaging system that includes CT and PET imaging systems, it should be understood that other imaging systems capable of performing the functions described herein are contemplated as being used.

Figure 1:
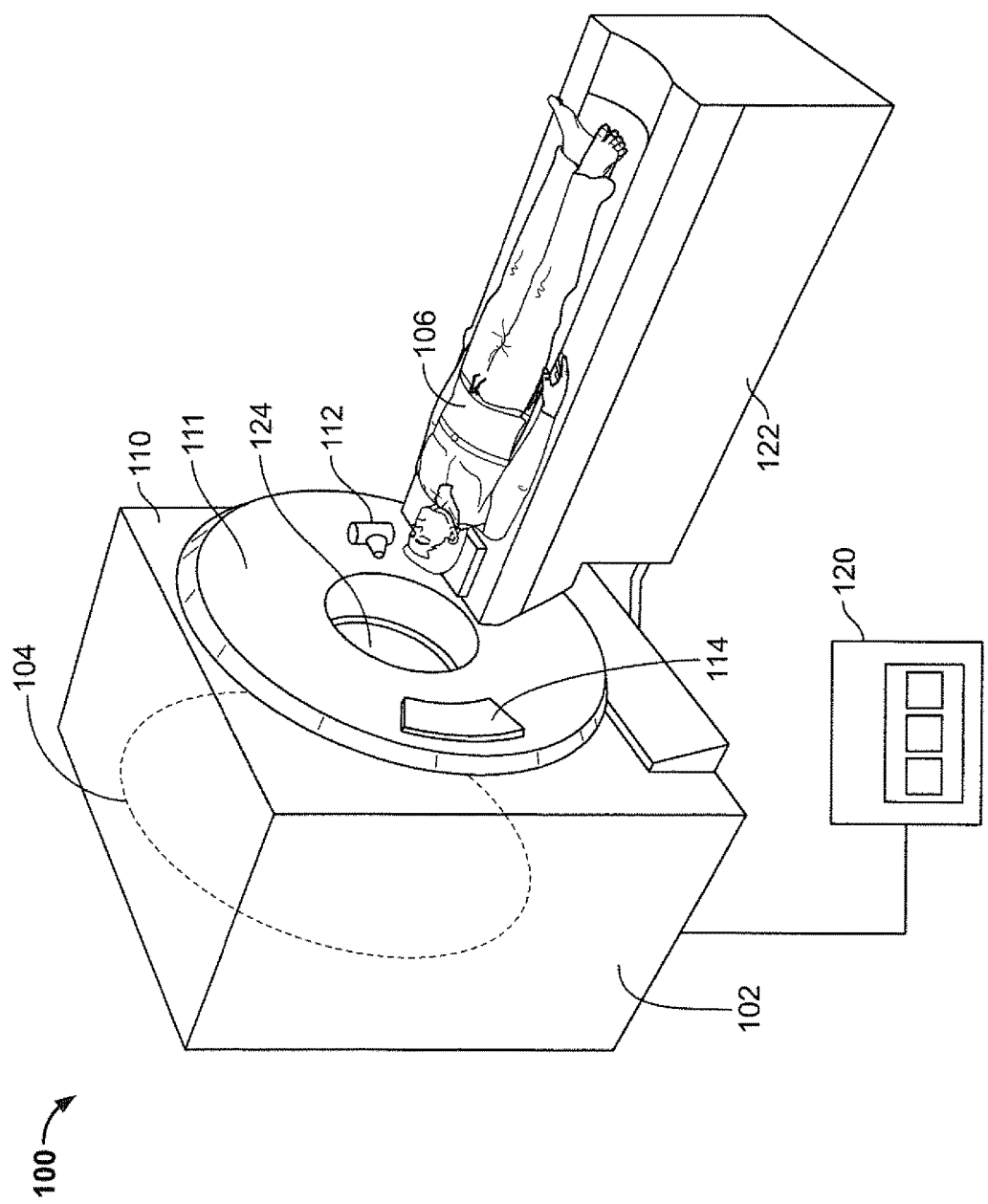
FIG. 1 is a diagram illustrating a dual-modality imaging system in accordance with various embodiments.

FIG. 1 is a diagram illustrating a dual-modality imaging system 100 in accordance with various embodiments. In one embodiment, the exemplary dual-modality imaging system 100 is a CT/PET imaging system. Optionally, modalities other than CT and PET are employed with the imaging system 100, as discussed above. For example, the imaging system 100 may be a standalone CT imaging system, a standalone PET imaging system, a magnetic resonance imaging (MRI) system, an ultrasound imaging system, an x-ray imaging system, a single photon emission computed tomography (SPECT) imaging system, an interventional C-Arm tomography system, CT systems for a dedicated purpose such as extremity or breast scanning, and combinations thereof, among others.

The CT imaging system generally includes a CT gantry 102 that includes a stationary portion 110 and a rotating portion 111. The stationary portion 110 provides a stable frame for the imaging system. The rotating portion 111 includes an x-ray source 112 that projects a beam of x-rays toward an x-ray detector 114 (e.g., detector array) on the opposite side of the rotating portion 111. The x-ray detector 114 in some embodiments includes a plurality of detector elements that are arranged in rows and channels that together sense the projected x-rays that pass through an object, such as a subject 106.

The rotating portion 111 also includes a bore therethrough. In various embodiments, the diameter of a gantry opening 124 (for the bore) and a bore depth of the CT gantry 102 define a bore volume. The bore depth is defined as the distance from one end of the bore at the gantry opening 124 to an opposite end of the bore (not shown in FIG. 1). For example, in one embodiment, the gantry opening 124 may be 80 centimeters in diameter. However, the gantry opening 124 and bore diameter may be different in other embodiments.

In various embodiments, the imaging system 100 also includes a PET gantry 104 (illustrated in phantom dashed lines) that allows a PET detector, such as a PET detector ring (not shown), to acquire emission data. The PET gantry 104 as described in more detail herein is configured to allow at least a portion of the PET detector to be within the housing of the CT gantry 102. In various embodiments, the PET gantry 104 may be partially or entirely within the CT gantry 102. It should be noted that the bore volume in various embodiments also includes the additional bore depth of the PET gantry 104. However, as described in more detail herein, different configurations herein allow for a large gantry opening 124 that may reduce the feeling of claustrophobia or other unease in patients, while reducing on overall footprint (e.g., depth) of the dual-modality imaging system 100.

In operation, operator supplied commands and parameters are used by a computer 120 to provide control signals and information to position a motorized table 122. More specifically, the motorized table 122 is utilized to move the subject 106 into and out of the imaging system 100. In particular, the motorized table 122 moves at least a portion of the subject 106 into the gantry opening 124 and extends into the CT gantry 102 and the PET gantry 104. While the table 122 moves the subject 106 through the gantry, the x-ray detector 114 and PET detector acquire image data that is used to generate images of the subject 106, such as using image reconstruction techniques in the art. For example, the computer 120 receives the image data, which is processed to generate a two-dimensional or three-dimensional image.

Various embodiments selectively position the detectors for acquiring PET images and CT images closer to one another to reduce the distance the motorized table 122, and hence the subject 106, must move into the bore. Reducing the distance between the CT detectors and the PET detectors facilitates co-registration, whereby the computer 120 combines images from the x-ray detector 114 with images from the PET detectors.

Figure 2:
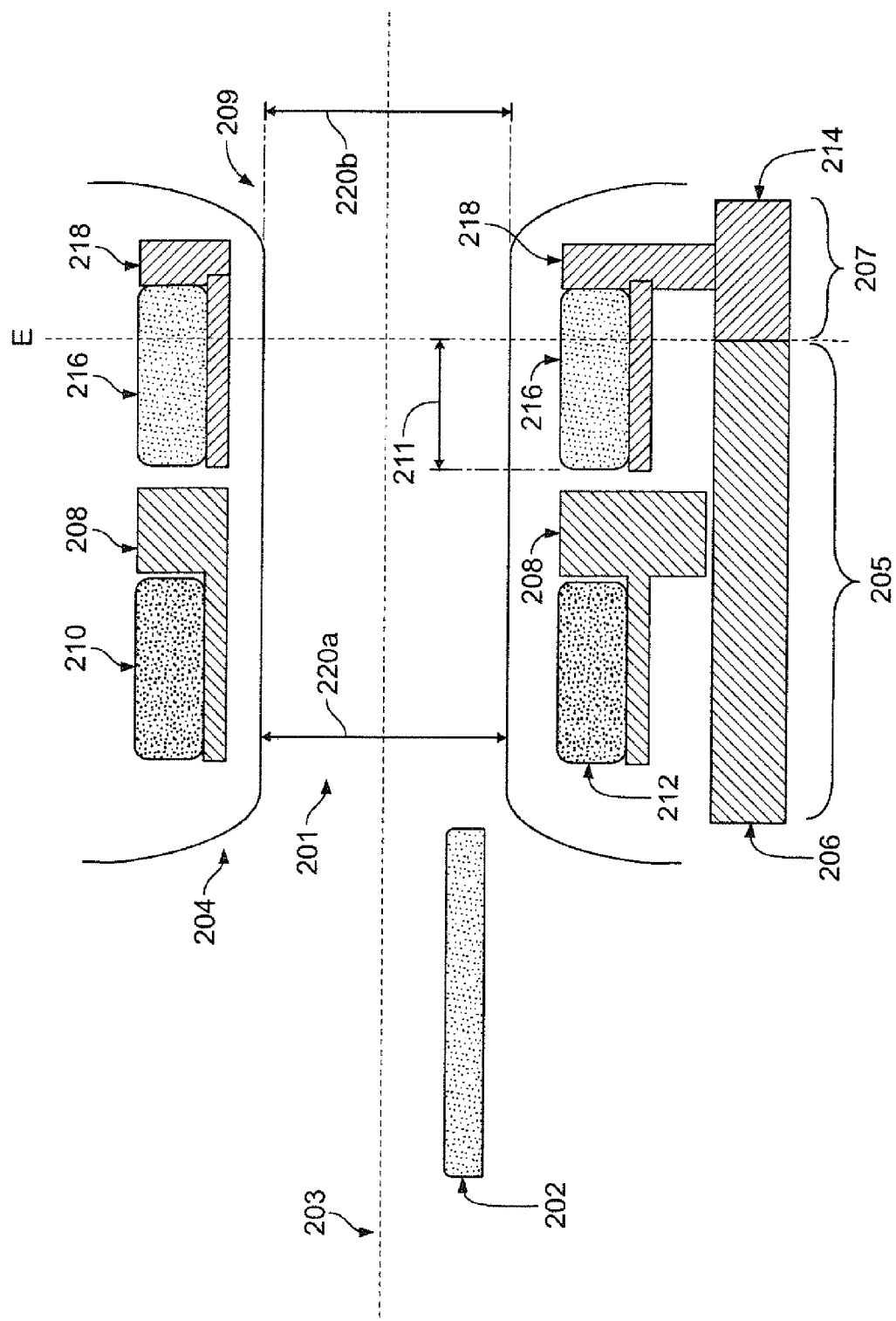
FIG. 2 is a cross-sectional schematic view of a dual modality imaging system with a uniform bore diameter in accordance with an embodiment.

FIG. 2 is a cross-sectional schematic view of a dual modality imaging system with a constant uniform bore diameter 220 in accordance with an embodiment. The imaging system 200 may be embodied as the imaging system 100 shown in FIG. 1. The imaging system 200 includes a motorized table 202, which may be controlled to move into a gantry opening 201. A housing 204 may cover a CT gantry 205 and a PET gantry 207. In another embodiment, the CT gantry 205 and the PET gantry 207 may include separate, distinct, housings that are coupled together.

The CT gantry 205 includes a stationary portion 206 and a rotating portion 208 separated by a slip ring (not shown). The rotating portion 208 includes an x-ray emitter 210 and an x-ray detector 212 (e.g., a detector array). The PET gantry 207 includes a support structure 214 and PET detectors 216 coupled thereto forming a PET detector ring 218. In another embodiment, the PET detectors 216 may form a partial ring of detectors. As can be seen in FIG. 2, the central axis of the PET detector ring 218 is aligned with the rotational axis of the rotating portion 208 of the CT gantry 205 to form an examination axis 203 therethrough that has a constant uniform bore diameter.

As illustrated in FIG. 2, the bore volume maintains a constant bore diameter 220a and 220b throughout the examination axis 203. Thus, the bore diameter 220a at the gantry opening 201 at one end of the housing 204 (e.g., entrance) is the same as the bore diameter 220b at the other end of the gantry 209. For example, in some embodiments, the bore diameter 220 may be approximately 80 centimeters.

However, in other embodiments, different diameters that are larger or smaller may be provided. In the illustrated embodiment, the housing 204 maintains a diameter of 80 centimeters throughout the entire length of the scan volume defined therein. Thus, in the illustrated embodiment, ac constant diameter bore is formed with the housing 204 dimensioned (e.g. sized and shaped) to cover or encase both the CT gantry 205 and the PET gantry 207.

In other embodiments, the bore diameter 220 (such as from 220a to 220b) may vary to accommodate an overlap in the PET detector ring 218 and the rotating portion 208 of the CT gantry as discussed in more detail in connection with FIGS. 3 and 4.

As can be seen in FIG. 2, the PET detector is illustrated as a PET detector ring 216 and extends at least partially into the CT gantry 205. The support structure 214 is configured to position the PET detector ring 216 adjacent to the CT detector 212 within the CT gantry 205 such that the PET detector ring 216 does not interfere (e.g., contact or abut) the slip ring or the rotating portion 208. For example, the PET detector ring 216 and CT detector 212 are spaced close to one another along the examination axis, but not in contact, which is a shorter distance than in conventional dual-modality systems having two gantries. Thus, the PET detector 216 may extend at least partially into the CT gantry 205 a distance 211.

In one embodiment, the PET detector ring 218 may be cantilevered from the support structure 214 of the PET gantry 207. For example, the support structure 214 may include one or more support members or arms to extend the PET detector ring 218 into the stationary portion 206 of CT gantry 205. The structural member may be fixed to support structure 214 and support the PET ring 218 along and about the examination axis 203. The support structure 214 may be configured having different shapes and sizes, for example, based on the configuration of the PET detector ring 218

In various embodiments, the support structure 214 and the CT gantry stationary portion 206 are fixedly coupled together. Fixedly coupled, as used herein in various embodiments, means that components are aligned and secured together. The support structure 214 may include, for example, an alignment member to facilitate fixedly coupling the support structure 214 to the CT gantry stationary portion 206 such that the PET gantry 214 is positioned with the examination axis of the CT detector and the PET detector ring 216 coincide to form the examination axis 203. For example, the alignment member may include prefabricated or machined plates with predefined markings and anchors to attach to the CT gantry stationary portion 206 to the PET support 214.

Figure 3:
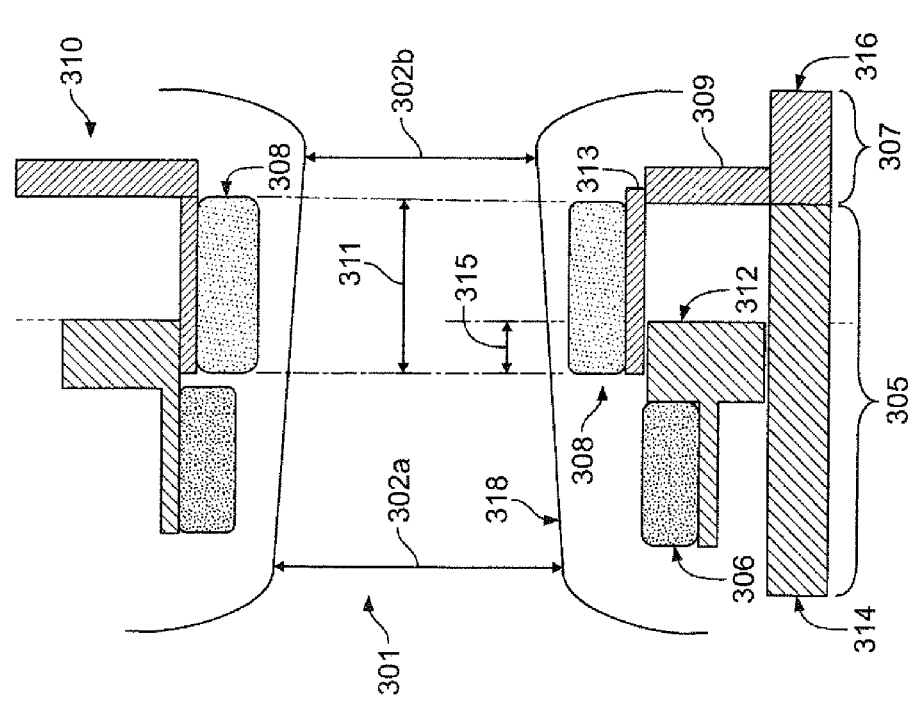
FIG. 3 is a cross-sectional schematic view of a dual modality imaging system with a varying bore diameter in accordance with an embodiment.

FIG. 3 is a cross-sectional schematic view of a dual-modality imaging system with a varying bore diameter in accordance with an embodiment. The imaging system 300 may be embodied as the imaging system 100 shown in FIG. 1. In one embodiment, the bore diameter 302a at the gantry opening 301 may be larger than the bore diameter 302b at the opposite end of the gantry structure. For example, the bore diameter 302a may be approximately 80 centimeters, whereas the bore diameter 302b may be approximately 70 centimeters. It should be appreciated that the bore diameters 302a and 302b may be larger or smaller, as well as having a different amount of change in bore diameter from one end to the other.

In one embodiment, a housing 318 may be selectively dimensioned (e.g., shaped) to accommodate the relative change in diameters 302a and 302b. For example, the housing 318 may taper radially such that a slanted bore wall is defined along the imaging axis as illustrated in FIG. 3. In another embodiment, the housing 318 may form stepwise configuration or curved wall (e.g., change shape or radius of curvature). In another embodiment, the CT gantry 305 and the PET gantry 307 may be configured with separate housings.

The imaging system 300 having a variable bore diameter provides space to overlap at least a portion of the PET detector 308 (e.g., PET detector ring) with the CT rotating portion 312. As illustrated in FIG. 3, the distance between the CT detector 306 and the PET detector 308 is reduced by extending the PET detector ring 308 further into the bore volume of the CT gantry 305 (as compared with the configuration illustrated in FIG. 2). The overlap distance 315 further reduces the distance 311 between the CT detector 306 and the PET detectors 308. In the illustrated embodiment, the PET gantry 316 is configured to extend and support the PET detector ring 308 radially inward (e.g., above) from the structural components of the rotating portion 312 as well as the stationary portion 314 of the CT gantry 305. Thus, components of the PET detector ring 308 may be positioned relative to CT detector ring to reduce the overlap distance 315.

As discussed herein in connection with FIG. 2, the CT gantry stationary portion 314 may be fixedly coupled with a support structure 316. When coupled, the rotational axis of the rotating portion 312 is aligned with the center of the PET detector ring 308. Optionally, an alignment member or mechanism may be included to facilitate alignment as described herein. As can be seen, the support structure 316 may include a vertical support 309 that is sized and shaped, and having a positioning support 313 (mounted to the vertical support 309) for supporting the PET detector ring 308 radially inward and above or within the rotating portion 312. Thus, in this embodiment, the PET detector ring 308 is still separated a distance from the rotating portion 312, but instead of spaced only axially from the rotating portion 312 (such as illustrated in FIG. 2), the PET detector ring 308 is also spaced radially inward from the rotating portion 312, with less axial offset. However, it should be appreciated that the radial and/or axial offset may be varied as desired or needed.

Figure 4:
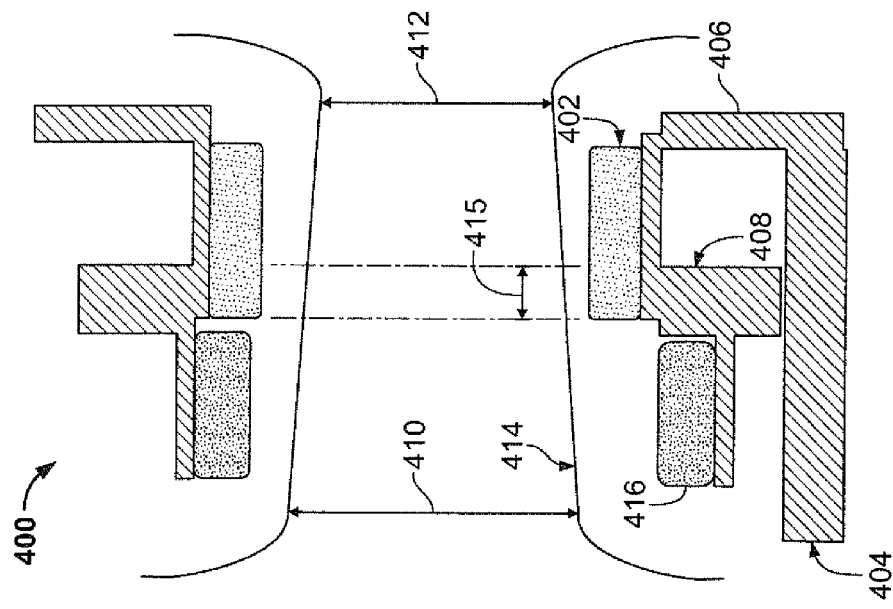
FIG. 4 is a cross-sectional schematic view of a dual modality imaging system with a common gantry in accordance with an embodiment.

In another embodiment, a PET detector ring may be fixedly coupled to the stationary portion of a CT gantry, thereby having a common gantry as illustrated in FIG. 4. A common gantry, as described herein, generally refers to a singly gantry to which the PET detector ring and the CT components are fixed.

FIG. 4 is a cross-sectional schematic view of a dual modality imaging system 400 with a common gantry 406 in accordance with an embodiment. In this embodiment, there is no separate PET gantry. Instead, the PET detector ring 402 is fixedly coupled to the CT stationary portion 404 of the CT gantry. The CT stationary portion 404 includes a structural member 406 that supports the PET detector ring 402 (to provide a similar alignment to the configuration illustrated in FIG. 3). In this embodiment, the CT stationary portion 404 may be configured with extra structural strength (e.g., supports) to allow both the PET detector ring 402 and a CT rotating portion 408 having a CT detector 416 to be mounted thereto. Thus, the PET detector ring 402 may be fixedly couple to the CT stationary portion 404.

Thus, the structural member 406 may position the PET detector ring 402 radially inward into the CT rotating portion 408, resulting in an overlap region 415 of the PET detector ring 402 and the CT rotating portion 408. Also as discussed above in connection with FIG. 3, the overlap 315 may result in a varying bore diameter and a shaped inner housing 414. However, it should be appreciated that in other embodiments, the PET detector 402 may not overlap with the CT detector ring 408. In these embodiments, as discussed in connection with FIG. 2, the housing 414 may maintain a constant uniform bore diameter.

Thus, in various embodiments, the PET detector is positioned inside the volume of the CT rotating gantry, in particular, right behind the CT detector in order to significantly reduce the FOV distance.

Figure 5:
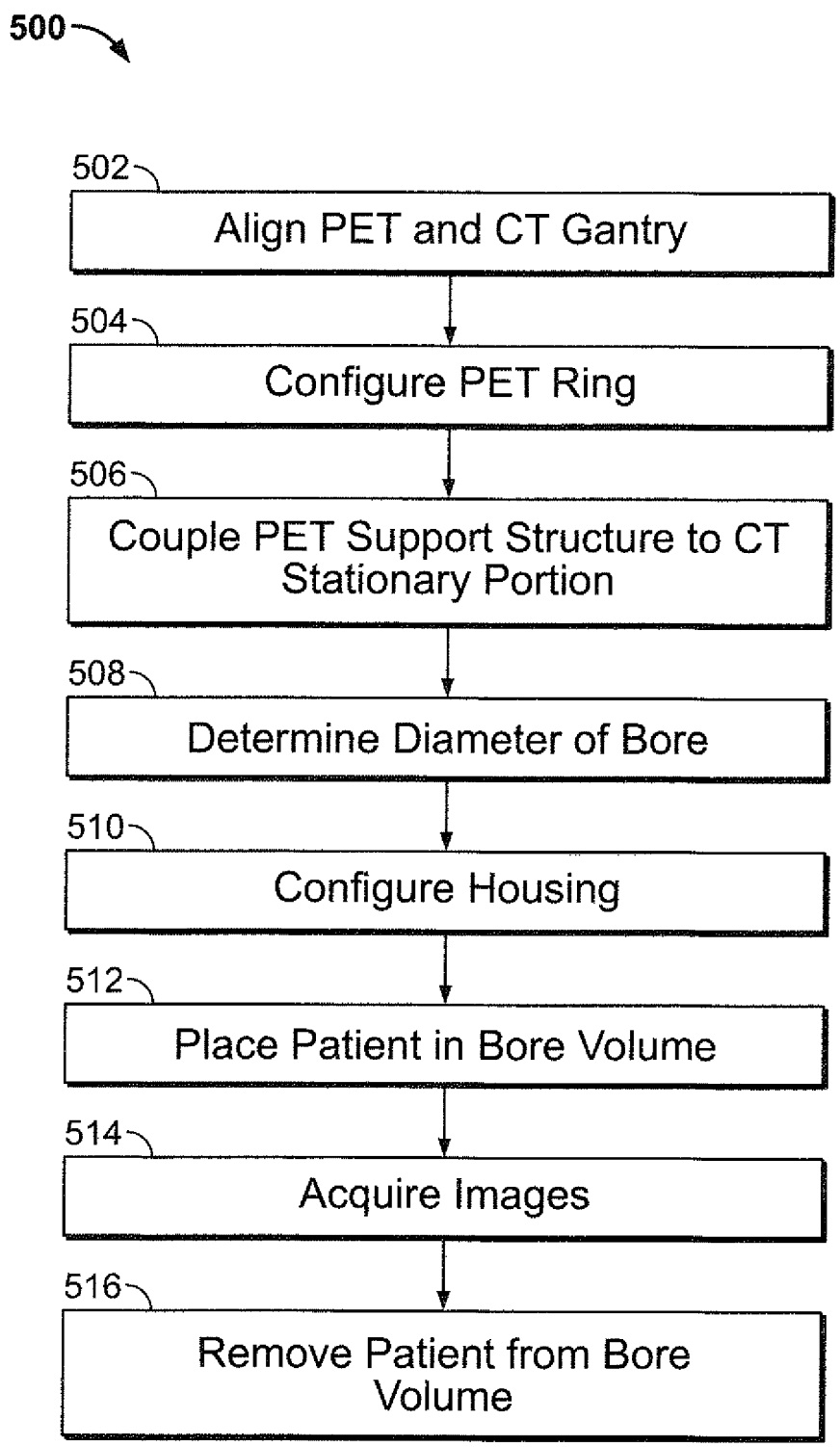
FIG. 5 is a flowchart of a method for configuring a dual-modality imaging system in accordance with various embodiments.

FIG. 5 is a flowchart of a method 500 for configuring a dual-modality imaging system. In one embodiment, the method may provide a combined PET and CT imaging system. The method 500 is described in connection with the embodiments of FIGS. 1 and 2. However, the method 500 is not limited to the configurations in those embodiments. Additionally, the steps of the method 500 may be performed in any order with some steps removed and/or other steps added. Additionally, the steps may be performed concurrently or sequentially.

At 502, the CT gantry 205 and the PET gantry 207 are aligned, for example, such that the axis of rotation of the rotating portion 208 aligns with the central axis of the PET ring 218 to form the imaging axis 203. It should be noted that any suitable process may be used as is known in the art to perform the alignment. In one embodiment, alignment members may be used to facilitate the alignment process.

At 504, the PET ring 218 is configured such that the PET ring 218 extends at least partially into the CT gantry 205. As illustrated in FIG. 2, at least a portion of the PET detector ring 218 extends within the CT gantry 205. In another embodiment, for example, as shown in FIG. 3, the PET detector 308 may be configured to have an overlapping distance 315 with the rotating portion of the CT detector 306.

At 506, the PET support structure 214 coupled to the CT stationary portion 206 as described herein. At 508, a diameter 220*a* at the gantry opening 201 and the diameter 220*b* at the other end of the gantry 209 is determined.

At 510, the housing 204 is configured in accordance with the diameters 220*a* and 220*b*. The housing 204 diameter may taper or be a constant uniform diameter based on the diameters 220*a* and 220*b*. The housing 204 may be selectively dimensioned (e.g., sized and shaped) based on the diameters 220*a* and 220*b*. It should be noted that in some embodiments, the housing 204 is prefabricated in one or multiple pieces based on the dimensional parameters of the system. The housing 204 thus covers the components therein and forms a smooth inner bore for receiving a patient therein.

At 512, a patient 106 is placed on the motorized table 202 and the computer 120 commands the motorized table 202 to move the patient 106 into the bore volume along the imaging axis 203. At 514, the computer 120 may acquire images from the CT detector 212 and/or the PET detectors 216. The computer 120 may then co-register the images to produce a combined image. At 516, the computer 120 commands the motorized table 202 to remove the patient 106 from the bore volume.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems. As another example, single modality systems may be employed in some embodiments.

Thus, various embodiments provide a multi-modality imaging system, such as a CT/PET system, that has a reduced bore length or examination axis.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof)

may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
   an x-ray computed tomography (CT) gantry having a rotating portion, a stationary portion, and a housing, the rotating portion and the stationary portion disposed within the housing, and the CT gantry including a bore volume through the rotating portion, the rotating portion of the CT gantry disposed radially inward of the stationary portion, and the rotating portion and stationary portion at least partially overlapping along an examination axis passing through the bore along a length of the bore;
   an x-ray source and an x-ray detector, wherein the x-ray source and the x-ray detector are coupled to the rotating portion and are configured to rotate with the rotating portion;
   a positron emission tomography (PET) support structure adjacent to the stationary portion of the CT gantry in an axial direction extending along the examination axis; and
   a PET detector, the PET detector coupled to the stationary portion of the CT gantry via the PET support structure, the PET detector extending at least partially into the CT gantry, such that at least a portion of the PET detector is within the housing of the CT gantry, the PET detector spaced axially along the examination axis along the length of the bore from the x-ray detector, the PET detector at least partially overlapping the stationary portion of the CT gantry along the examination axis.

2. The imaging system of claim 1, wherein the PET detector is a PET detector ring and further comprising a PET gantry, wherein the PET gantry is fixedly coupled to the stationary portion of the CT gantry.

3. The system of claim 2, wherein the PET detector ring is cantilevered in the axial direction from the PET gantry to extend at least partially into the CT gantry, wherein the PET detector at least partially overlaps the rotating portion of the CT gantry in the axial direction.

4. The system of claim 2, wherein the PET gantry is positioned entirely within the housing of the rotating portion of the CT gantry.

5. The imaging system of claim 1, wherein the bore volume maintains a constant uniform bore diameter along the examination axis from one end of the bore volume to an opposite end of the bore volume.

6. An imaging system comprising:
   an x-ray computed tomography (CT) gantry having a rotating portion, a stationary portion, and a housing, the rotating portion and the stationary portion disposed within the housing, the CT gantry including a bore volume through the rotating portion, the rotating portion of the CT gantry disposed radially inward of the stationary portion, and the rotating portion and stationary portion at least partially overlapping along an examination axis passing through the bore along a length of the bore;
   an x-ray source and an x-ray detector, wherein the x-ray source and the x-ray detector are coupled to the rotating portion and are configured to rotate with the rotating portion;
   a positron emission tomography (PET) support structure adjacent to the stationary portion of the CT gantry in an axial direction extending along the examination axis; and
   a PET gantry having a PET detector ring coupled thereto, the PET gantry coupled to the stationary portion of the CT gantry via the PET support structure, the PET detector ring extending at least partially into the CT gantry, such that at least a portion of the PET detector ring is within the housing of the CT gantry, the PET detector ring spaced axially along the examination axis along the length of the bore from the x-ray detector, the PET detector ring at least partially overlapping the stationary portion of the CT gantry along the examination axis.

7. The imaging system of claim 6, wherein the bore volume maintains a uniform bore diameter along an examination axis from one end of the bore volume to an opposite end of the bore volume.

8. The imaging system of claim 6, wherein the bore volume has a changing bore diameter along the examination axis from one end of the bore volume to an opposite end of the bore volume.

9. The system of claim 6, wherein the PET detector ring is cantilevered in the axial direction from the PET gantry to extend at least partially into the CT gantry, wherein the PET detector ring at least partially overlaps the rotating portion of the CT gantry in the axial direction.

10. The system of claim 6, wherein the PET gantry is positioned entirely within the housing of the CT gantry.

11. The imaging system of claim 6, wherein the PET detector ring is positioned to at least partially overlap with the rotating portion along an examination axis defined from one end of the bore volume to an opposite end of the bore volume.

12. The imaging system of claim 6, wherein the PET detector ring is positioned radially inward from the x-ray source and an x-ray detector.

13. The imaging system of claim 6, wherein the housing is a single housing structure having the CT gantry and PET gantry therein.

14. An imaging system comprising:
an x-ray computed tomography (CT) gantry having a rotating portion, a stationary portion, and a housing, the rotating portion and the stationary portion disposed within the housing, the CT gantry including a bore volume through the rotating portion, the bore volume having a constant diameter along a length of an examination axis through the CT gantry, the rotating portion of the CT gantry disposed radially inward of the stationary portion, and the rotating portion and the stationary portion at least partially overlapping along an examination axis passing through the bore along a length of the bore;
an x-ray source and an x-ray detector, wherein the x-ray source and the x-ray detector are coupled to and rotating with the rotating portion of the CT gantry;
a positron emission tomography (PET) support structure adjacent to the stationary portion of the CT gantry in an axial direction extending along the examination axis; and
a PET detector ring coupled to the stationary portion of the CT gantry via the PET support structure, the PET detector ring extending at least partially into the CT gantry, the PET detector ring spaced axially along the examination axis along the length of the bore from the x-ray detector, the PET detector ring at least partially overlapping the stationary portion of the CT gantry along the examination axis.

15. The system of claim 14, wherein the PET detector ring is cantilevered in the axial direction from the PET support structure to extend at least partially into the CT gantry.

16. The system of claim 14, wherein the PET detector ring is positioned entirely within the housing of the CT gantry.

17. The imaging system of claim 14, wherein the PET detector ring is positioned to at least partially overlap with the rotating portion along the examination axis defined from one end of the bore volume to an opposite end of the bore volume.

18. The imaging system of claim 14, wherein the PET detector ring is positioned axially offset from the rotating portion.

19. The imaging system of claim 14, wherein the housing is a single housing structure having the CT gantry and PET detector ring therein.

20. The imaging system of claim 14, wherein a central axis of the PET detector ring is aligned with a rotational axis of the rotating portion.

* * * * *